United States Patent
Miura et al.

(12) 
(10) Patent No.: US 6,228,998 B1
(45) Date of Patent: *May 8, 2001

(54) AMINO SPACERED GLYCOSAMINOGLYCAN DERIVATIVES AND THEIR USE IN COPOLYMERIZATION WITH ACRYLAMIDE

(75) Inventors: Ryu Miura; Sadako Yamagata; Tatsuya Yamagata, all of Kanagawa (JP)

(73) Assignee: Seikagaku Kogyo Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/504,675

(22) Filed: Jul. 20, 1995

(30) Foreign Application Priority Data

Jul. 22, 1994 (JP) .................................................... 6-191285

(51) Int. Cl.[7] .................................................. C07H 5/04
(52) U.S. Cl. ...................... 536/22.1; 536/18.7; 536/20; 536/21; 536/29.1; 536/122; 536/123; 536/123.1
(58) Field of Search ................. 435/18, 24; 525/50, 525/54.1; 536/4.1, 18.7, 20, 21, 22.1, 29.1, 122, 123, 123.1; 530/345, 814; 514/54–56

(56) References Cited

U.S. PATENT DOCUMENTS

| | | | |
|---|---|---|---|
| 5,198,355 | * 3/1993 | Kikuchi et al. | 435/232 |
| 5,310,881 | * 5/1994 | Sakurai et al. | 530/395 |
| 5,332,812 | * 7/1994 | Nicolson et al. | 536/21 |

FOREIGN PATENT DOCUMENTS

| | | |
|---|---|---|
| 0 087 995 | * 7/1983 | (EP) . |
| 0087995 | 9/1983 | (EP) . |
| 0 244 932 | * 11/1987 | (EP) . |
| 0244932 | 11/1987 | (EP) . |
| 0454898 | 11/1991 | (EP) . |
| 0493622 | 7/1992 | (EP) . |

OTHER PUBLICATIONS

Miura et a., "Analysis of Glycosaminoglycan–Degrading Enzymes by Substrate Gel Electrophoresis (Zymography)", Anaytical Biochemistry, vol. 225, No. 2, pp. 333–340, Mar. 1995.*

Raja et al., "Preparation of Alkylamine and [125]I–Radiolabeled Derivatives of Hyaluronic Acid Uniquely Modified at the Reducing End", Analytical Biochemistry, vol. 139, pp. 168–177, 1984.*

Fiszer–Szafarz, "Hyaluronidase Polymorphism Detected by Polyacrylamide Gel Electrophoresis. Application to Hyaluronidases from Bacteria, Slime Molds, Bee and Snake Venoms, Bovine Testes, Rat Liver Lysosomes, and Human Serum", Analytical Biochemistry, 143:76–81 (1984).

Laemmli, "Cleavage of STructural Proteins Proteins During the Assembly of the Head of Bacteriophage T4", Nature, 227:680–685 (1970).

Steiner et al, "A Zymographic Assay for Detection of Hyaluronidase Activity on Polyacrylamide Gels and Its Application to Enzymatic Activity Found in Bacteria", Analytical Biochemistry, 200:405–410 (1992).

Guntenhöner et al, "A Substrate–Gel Assay for Hyaluronidase Activity", Matrix, 12:388–396 (1992).

Miura et al, "Analysis of Glycosaminoglycan–Degrading Enzymes by Substrate Gel Electrophoresis (Zymography)", Analytical Biochemistry, 225:333–340 (1995).

* cited by examiner

Primary Examiner—Howard C. Lee
(74) Attorney, Agent, or Firm—Sughrue, Mion, Zinn, Macpeak & Seas, PLLC (57) ABSTRACT

A glycosaminoglycan derivative is disclosed wherein a first amino group of a spacer compound ($NH_2$—Y—$NH_2$) is bonded to an aldehyde formed by reducing and partially oxidizing a reducing end sugar of a glycosaminoglycan, via an aminoalkyl bond, or a lactone formed by oxidizing and cyclodehydrating the reducing end sugar of a glycosaminoglycan, via an acid amide bond, and further a hydrocarbon compound having a allyl group at one end and a functional group at another end which is bonded to the second amino group of the spacer compound. This derivative is useful as a substrate in a process for identifying a glycosaminoglycan-degrading enzyme that gives good reproducibility and sensitivity.

14 Claims, 6 Drawing Sheets

AMINO SPACERED GLYCOSAMINOGLYCAN DERIVATIVES AND THEIR USE IN COPOLYMERIZATION WITH ACRYLAMIDE

FIELD OF THE INVENTION

This invention relates to a novel derivative of a glycosaminoglycan in which an allyl compound is bonded to a reducing end sugar of a glycosaminoglycan via an aminoalkyl bond or an acid amide bond. It further relates to a glycosaminoglycan-bonded polyacrylamide gel in which the above-mentioned novel derivative is copolymerized with acrylamide. It furthermore relates to a process for identifying a glycosaminoglycan-degrading enzyme using the above-mentioned polyacrylamide gel as a gel electrophoresis carrier.

BACKGROUND OF THE INVENTION

There have been known glycosaminoglycan-bonded substances formed by binding various substances (for example, proteins, phospholipids, lipids and the like) to a hemiacetal of a reducing end sugar of a glycosaminoglycan optionally activated. Attempts have been made to apply these substances to drugs (JP-A-3-284698 corresponding to EP-A-454898, International Publication No. WO92/01720 corresponding to EP-A-493622; the term "JP-A" as used herein means an "unexamined published Japanese patent application").

Also, slight changes in the amount or microstructure of glycosaminoglycans have attracted public attention with regard to the infection with bacteria or viruses, cancer, hereditary diseases, etc. These changes frequently depend on glycosaminoglycan-degrading enzymes occurring in a trace amount in cells, tissues and body fluids. Accordingly, it has been regarded as important to assay these enzymes.

It is not suitable for assaying glycosaminoglycan-degrading enzymes to use such a method as those employed in assaying glycosidase, i.e., one comprising using a substrate consisting of a monosaccharide or an oligosaccharide and a chromogenic compound or a fluorescent compound bonded thereto and observing and measuring the rate and the manner of appearance or disappearance of the color development (or fluorescence) due to the digestion with the enzymes. Thus, these enzymes have been assayed by using a glycosaminoglycan as a substrate and determining the disaccharide or oligosaccharide formed by digestion or examining a decrease in the molecular weight. There has been known a gel electrophoretic method for assaying a protease or the like which is called "zymography" and comprises electrophoresing an enzyme on a gel having a substrate uniformly embedded therein and, after the digestion of the substrate with the enzyme, measuring the loss in the substrate. In this method, however, high molecular weight compounds are exclusively usable as the substrate, since a low molecular weight substrate per se would be electrophoresed and thus flow out from the gel. Moreover, these methods are disadvantageous in that a complicated operation is required, sensitivity and reproducibility are poor and applicable substrates are limited.

SUMMARY OF THE INVENTION

An object of the present invention is to provide a process for identifying a glycosaminoglycan-degrading enzyme which is free from the above-mentioned problems. The present invention also provides a novel glycosaminoglycan derivative which is useful as a substrate in the above-mentioned process as well as an electrophoresis gel carrier composed of a copolymer of this novel derivative and acrylamide.

Under these circumstances, the present inventors have conducted extensive studies in order to easily and accurately assay a trace amount of a glycosaminoglycan-degrading enzyme with a high sensitivity, and as a result, the present invention has been completed.

Accordingly, the gist of the present invention resides in: 1) a glycosaminoglycan derivative in which a compound having an allyl group at one end which is not concerned in bonding with a glycosaminoglycan is bonded to a reducing end sugar of said glycosaminoglycan via an aminoalkyl bond or an acid amide bond, more specifically said reducing end sugar is an aldehyde group formed by reducing and partially oxidizing the reducing end sugar of a glycosaminoglycan, or a lactone formed by oxidizing and cyclodehydrating the reducing end sugar of a glycosaminoglycan, or a glycosaminoglycan derivative in which a spacer compound having at least two amino groups is bonded to an aldehyde group or a lactone formed as described above via an aminoalkyl bond or an acid amide bond, respectively, and further a hydrocarbon compound having an allyl group at one end and a functional group capable of binding to an amino group at another end and having or not a heteroatom in the chain, is bonded to the amino group of said spacer compound; 2) a glycosaminoglycan-bonded polyacrylamide gel which is a copolymer composed of the glycosaminoglycan derivative as described above and acrylamide as constituting monomers; and 3) a process for the identification of a glycosaminoglycan-degrading enzyme which comprises electrophoresing a specimen containing the glycosaminoglycan-degrading enzyme by using the glycosaminoglycan-bonded polyacrylamide gel as described above as a carrier, after the electrophoresis, incubating the carrier under such conditions as to proceed the enzymatic reaction, and then detecting the degradation of the glycosaminoglycan fixed to the carrier to thereby separate and identify the glycosaminoglycan-degrading enzyme in the specimen.

DETAILED DESCRIPTION OF THE INVENTION

The particular glycosaminoglycan employed in the present invention is not critical thereto and depends upon the purpose thereof. Specifically, examples thereof include chondroitin, chondroitin sulfate, hyaluronic acid, dermatan sulfate, heparin, heparan sulfate, keratan sulfate, kerato polysulfate and the like. Among these glycosaminoglycans, chondroitin sulfate, dermatan sulfate, heparin, keratan sulfate and heparan sulfate are preferable and chondroitin sulfate is particularly preferable.

An aldehyde group is formed by reducing a reducing end sugar of a glycosaminoglycan followed by partial oxidization. To perform this reaction, a known method, for example, the one described in EP-A-454898, may be appropriately employed. The reduction is carried out, for example overnight, in a mixed solution comprising a buffer, for example, a borate buffer (pH 8.3), a phosphate buffer (pH 8.6) or the like, with an organic solvent, for example, dimethylformamide, acetonitrile or the like, at a temperature of from 0 to 40° C., preferably from 15 to 20° C., using a reducing agent such as an alkali boron hydride salt, for example, sodium boron hydride, sodium boron cyanohydride or the like, in an amount of 5 to 50 molar equivalent, preferably 10 to 20 molar equivalent, per mole of a glycosaminoglycan. The subsequent oxidation is carried out at a temperature of from 0 to 20° C., preferably from 0 to 5° C. using an oxidizing agent such as an alkali periodate, for example, sodium periodate, potassium periodate or the like, in an amount of 1 to 30 molar equivalent, preferably 5 to 10 molar equivalent, per mole of the reduction product.

Similarly, the formation of lactone through the oxidization of the reducing end sugar of the glycosaminoglycan followed by cyclodehydration may be performed by using a method described in the above-mentioned patent. More particularly, the reducing end sugar is first cleaved by oxidation. This oxidation is performed in such a solution as described above at a temperature of from 0 to 40° C., preferably from 15 to 20° C., by using an oxidizing agent such as iodine, bromine or the like in an amount of 2 to 20 molar equivalent, preferably 5 to 15 molar equivalent, per mole of a glycosaminoglycan. The oxidized product is then cyclodehydrated by treating with an acid. As the acid, use can be made of a solid acid such as a strongly acidic cation exchange resin, for example, Dowex 50 (manufactured by Dow Chemical Co.) or Amberlite IR120 (manufactured by Rohm & Haas Co.).

The aldehyde group or the lactone of the glycosaminoglycan formed by activating the reducing end sugar is then reacted with a spacer compound having at least two amino groups. The spacer compound is represented by the following formula (1):

$$NH_2\text{—}Y\text{—}NH_2 \qquad (1)$$

wherein Y represents $-[(CH_2)_n-(CHR)_m]-$, $-(CH_2)_x-CH(COOH)-$, phenylene or naphthylene; R represents H or alkyl having 1 to 4 carbon atoms; x is an integer of 3 or 4; m is an integer of from 1 to 10; and n is an integer of from 1 to 10, provided that m+n is not more than 10.

Specific examples of such a compound include α,ω-alkylenediamines such as ethylenediamine, 1,3-propanediamine (trimethylenediamine), 1,4-butanediamine (tetramethylenediamine; putrescine), 1,6-hexanediamine (hexamethylenediamine), 1,6-diamino-2-ethylhexane and the like, aromatic diamines such as 1,4-diaminobenzene, 1,4-diaminonaphthalene, 1,5-diaminonaphthalene, 2,7-diaminonaphthalene and the like and basic amino acids such as lysine, ornithine and the like. Among these compounds, α,ω-alkylenediamines are preferable and ethylenediamine is particularly preferable.

The reaction with the aldehyde group can be performed by a reductive amination reaction known per se. Namely, the aldehyde group is reacted with an amino group to thereby form a Schiff base. Then this Schiff's base is reduced and bonded to an amino alkyl ($-CH_2NH-$) group. For example, in such a solvent as employed in the above reaction, the oxidized glycosaminoglycan is reacted with about 150 molar equivalent of the diamino compound at a temperature of from 15 to 60° C. for several ten minutes to several ten hours, preferably about 5 hours. At the same time or thereafter, reduction is performed by using a reducing agent such as sodium boron cyanohydride, sodium boron hydride or a volatile borane complex, for example, borane dimethylamine complex, borane triethylamine complex, borane pyridine complex or the like, in an amount of 10 to 100 moles per mole of the oxidized glycosaminoglycan.

The reaction with the lactone may be performed by reacting the lactone in the form of a trialkylamine salt with the diamino compound. Alternatively, a mixture of the lactone with the diamino compound is adjusted to pH 4 to 7 by using an alkali such as an aqueous solution of sodium hydroxide and then reacted at a temperature of from 0 to 70° C., preferably from 15 to 50° C. Thus, an acid amide bond can be formed.

Next, the free amino group of the aminated glycosaminoglycan thus formed is reacted with a hydrocarbon compound (hereinafter sometimes referred to as an amino group-reactive allyl compound) having an allyl group at one end and a functional group capable of binding to an amino group at another end and having or not a heteroatom, such as O, S or NH, in the binding chain, to thereby synthesize an allyl group-containing glycosaminoglycan derivative. The hydrocarbon moiety is preferably acyclic, more preferably linear.

The functional group capable of binding to an amino group may be any group so long as it has a reactivity with an amino group. Examples thereof include an epoxy group, a halogen atom, a hydroxyl group, a carboxyl group and the like. By taking the reactivity, by-product, etc. into consideration, it is preferable to use an epoxy group. A compound having an epoxy group and an allyl group is exemplified by those obtained by reacting an alcohol having an allyl group with epichlorohydrin. The most preferable example thereof is allylglycidyl ether (allyl 2,3-epoxypropyl ether).

This reaction is performed in an aqueous solvent, for example a mixed solvent containing water and lower alcohol having 1 to 4 carbon atoms, at a temperature of from 0 to 70° C., preferably from 15 to 50° C., for several ten minutes to several ten hours, preferably 1 to several hours, using about 1,600 molar equivalent of allylglycidyl ether.

In the above-mentioned method, the glycosaminoglycan activated in the reducing end sugar is reacted with the diamine compound and subsequently with the amino group-reactive allyl compound to thereby synthesize the allyl group-containing glycosaminoglycan derivative. Alternatively, the activated glycosaminoglycan may be reacted with a compound having an allyl group at one end and an amino group at another end, for example, allylamine, N-allylthio-urea or N-allylurea, to thereby synthesize an allyl group-containing glycosaminoglycan derivative. Conditions for this reaction can be easily determined by those skilled in the art through a preliminarily experiment.

After the reaction, the target compound is separated from the reaction mixture through precipitation from an alcohol, etc. and purified by known purification techniques, such as dialysis, ion exchange chromatography or the like, followed by lyophilization under reduced pressure.

In accordance with the above-mentioned method, allylglycidyl ether is bonded to a glycosaminoglycan via ethylenediamine. The product thus obtained is represented by the following formula (2):

(2)

wherein GAG-R'— represents glycosaminoglycan residue being modified at the reducing end sugar; and R' represents $CH_2$ or CO.

In the present invention, a gel electrophoresis carrier is synthesized by using the allyl group-containing glycosaminoglycan derivative.

The carrier can be synthesized in accordance with a conventional method for preparing a polyacrylamide gel. Namely, the allyl group-containing glycosaminoglycan derivative is added to an aqueous solution containing acrylamide and N,N'-methylenebisacrylamide (Bis). The obtained mixture is homogeneously mixed by, for example, allowing to stand in a dark and cold place over day and night. Then it is polymerized using a polymerization initiator such as peroxide, for example persulfate, benzoyl peroxide or the like, or azo compound, for example azobisisobutyronitrile or the like, or a redox polymerization initiator containing an oxidizing agent and a reducing agent. It is also possible to add N,N,N',N'-tetramethylethylenediamine (TEMED) as a polymerization accelerator. To the acrylamide, the N,N'-methylenebisacrylamide may be used at such a ratio as employed in ordinary polyacrylamide gels. The allyl group-containing glycosaminoglycan derivative is generally used in an amount of from 1 to 20 µg/ml, though it varies depending on the glycosaminoglycan substrate employed. The polymerization is performed in a cell adequate for the size of the gel to be synthesized.

In the present invention, a trace amount of a glycosaminoglycan-degrading enzyme is electrophoresed using the glycosaminoglycan-bonded polyacrylamide gel as a carrier under such conditions that the substrate is not degraded by the enzyme. The buffer for the electrophoresis is appropriately prepared depending on the degrading enzyme and the substrate employed. After the electrophoresis, the carrier is washed with the buffer, etc., if necessary, and then allowed to stand under the conditions suitable for the enzyme reaction. The reaction conditions, including buffer, pH, temperature and time, may be appropriately determined by taking the types of the degrading enzyme into consideration. After the reaction, the carrier is subjected to color-development using a chromogenic reagent such as Alcian Blue, Toluidine Blue or the like. When the substrate bonded to the polyacrylamide gel is digested by the enzyme, the degraded product, which does not undergo color development but remains white, can be detected. Thus the activity of the degrading enzyme can be identified.

Accordingly, glycosaminoglycan-degrading enzymes differing in substrate specificity can be easily separated or identified by synthesizing gel carriers having different glycosaminoglycans bonded thereto and electrophoresing the enzymes by using these carriers. This process is applicable to an enzyme contaminated with inhibitors or impurities or a specimen containing two or more degrading enzymes and, moreover, the isolation or identification can be easily and accurately performed with a high sensitivity.

In the process of the present invention, use can be made of chondroitin, chondroitin sulfate, hyaluronic acid, dermatan sulfate, heparin, heparan sulfate and keratan sulfate as the glycosaminoglycan. Thus this process is highly useful in the identification of enzymes capable of degrading these glycosaminoglycans. It is particularly advantageous in that a degrading enzyme for a glycosaminoglycan having a lower molecular weight than hyaluronic acid, for example, chondroitin sulfate, which cannot be isolated or identified by using the conventional polyacrylamide gel, can be isolated or identified thereby.

The novel glycosaminoglycan derivative of the present invention having an allyl group in its molecule can be easily copolymerized with acrylamide to thereby give a glycosaminoglycan-bonded copolymer. A glycosaminoglycan-degrading enzyme such as chondroitin sulfate-degrading enzyme can be identified using as a carrier this copolymer gel having fixed therein a glycosaminoglycan such as chondroitin sulfate which has a relatively low molecular weight and thus can be hardly fixed in a conventional polyacrylamide gel but flow out therefrom during electrophoresis. The other examples of the glycosaminoglycan-degrading enzymes which can be identified by the method of the present invention include heparin- or heparan sulfate-degrading enzyme, dermatan sulfate-degrading enzyme and keratan sulfate-degrading enzyme.

By the electrophoresis using the copolymer gel of the present invention, an enzyme can be isolated from its inhibitors and impurities. Also, two or more degrading enzymes can be separated from each other thereby. Thus a glycosaminoglycan-degrading enzyme can be easily detected, isolated and identified with a high sensitivity.

Accordingly, it is expected that a novel enzyme might be found out by electrophoresing cell tissues, body fluids, blood, etc. using copolymer gels having various glycosaminoglycans bonded thereto. There is a high possibility that an enzyme isomer, which cannot be found out by the conventional methods, might be detected, separated and identified and, in its turn, its relation to diseases or inflammation might be clarified.

To further illustrate the present invention in greater detail, and not by way of limitation, the following Examples will be given.

EXAMPLE 1

Preparation of Chondroitin Sulfate-allyl Compound

Four thousand mg (0.2 mmol) of chondroitin sulfate (molecular weight: 20,000) was dissolved in 40 ml of a 50 nM sodium borate buffer (pH 8.3). Then 30.26 mg (0.8 mmol) of sodium boron hydride was added thereto and the mixture was reacted at room temperature for 20 hours. After adjusting the pH value to 4.0 with acetic acid, the reaction mixture was dialyzed against water at 4° C. and lyophilized. A reducing end sugar reduction product was obtained as a white powder.

Four thousand mg (0.2 mmol) of the reduction product (reduced chondroitin sulfate; molecular weight: 20,000) was dissolved in 40 ml of 40 mM imidazole hydrochloride (pH 6.5). Then 171 mg (0.8 mmol) of sodium periodate was added thereto and the mixture was reacted in the dark at 0° C. for 1 hour. The resulting reaction mixture was dialyzed against water at 4° C. and lyophilized. The white powder thus obtained was a product which had been oxidized exclusively at the reducing end sugar and had an aldehyde group (chondroitin sulfate-aldehyde).

Four thousand mg (0.2 mmol) of the chondroitin sulfate-aldehyde was dissolved in 50 ml of water and 15 ml of 2 M ethylenediamine was added thereto. After 15 minutes, 1.26 g (20 mmol) of sodium boron cyanohydride was added and the resulting mixture was reacted at room temperature for 5 hours. Next, 189 mg (5 mmol) of sodium boron hydride was added and the mixture was reacted for 1 to 4 days. The resulting reaction mixture was dialyzed against water at 4° C. and lyophilized. The white powder thus obtained was a product having amino group (aminated chondroitin sulfate).

Purity of aminated chondroitin sulfate (determined by ninhydrin reaction using glucosamine as standard): 95.2%.

One hundred mg of the aminated chondroitin sulfate was dissolved in 2 ml of water and 1 ml of ethanol was added thereto. After adding 1 ml of allylglycidyl ether (allyl 2,3-epoxypropyl ether), the mixture was reacted at 40° C. for 2 hours. The resulting reaction mixture was dialyzed against water at 4° C. and lyophilized. A chondroitin sulfate-allyl compound was obtained as a white powder in a yield of 98 mg.

Purity of chondroitin sulfate-allyl compound was 95.3% [determined by calculating the content of allyl group based on the ratio of a proton of N-acetyl group of chondroitin sulfate (2 ppm) to three protons of allyl group (5–6 ppm) in NMR)].

Figure 1:
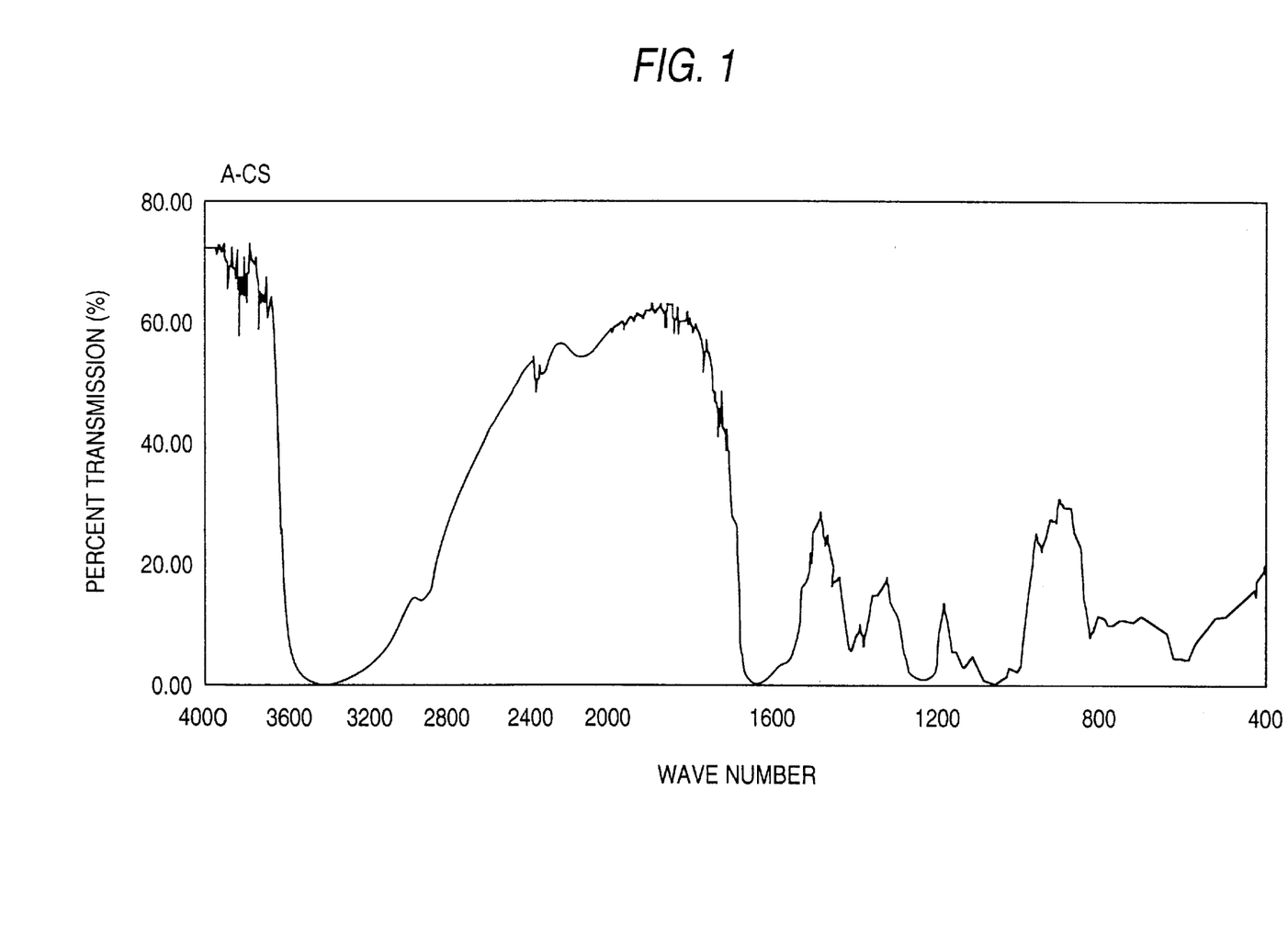
FIG. 1 is an IR spectrum of the chondroitin sulfate-allyl compound of the present invention.

The optical rotation of this compound was −25.16 (1%, H2O) and its IR spectrum is shown in FIG. 1.

EXAMPLE 2

Twenty-five g of chondroitin sulfate (molecular weight: 20,000) was dissolved in 2,500 ml of water. Then, 2,500 ml of a solution of 5 g of iodine in methanol was added thereto and the mixture was reacted for 20 hours. The reaction mixture was concentrated to 300 ml under reduced pressure and ethanol was added to thereby give a white precipitate (a reducing end sugar reduction product). The resulting product was dissolved in 1 liter of water and passed through 1 liter of Dowex 50(H$^+$) to give an acidic fraction. This acidic fraction was concentrated to 500 ml under reduced pressure and 500 ml of dimethylformamide (DMF) was added thereto followed by reconcentration. After repeating this procedure thrice or more, a DMF solution was obtained. Then it was allowed to stand at 4° C. for 20 hours to give a reducing end sugar lactonized product of chondroitin sulfate.

To a solution of this chondroitin sulfate lactone in DMF (4,000 mg/50 ml) was added 1.8 g of ethylenediamine. After reacting, the reaction mixture was dialyzed against water and lyophilized. An aminated chondroitin sulfate was obtained as a white powder.

Purity of aminated chondroitin sulfate: 94.7%.

One hundred mg of this aminated chondroitin sulfate was reacted with allyl glycidyl ether in accordance with the procedure of Example 1. Thus 96.7 mg of the product was obtained.

Purity of chondroitin sulfate-allyl compound: 95.0%.

Optical rotation: −25.0 (1%, H$_2$O).

EXAMPLE 3
Preparation of Heparin-allyl Compound

Starting from 700 mg (0.2 mmol) of heparin (molecular weight: 3,500), the procedure of Example 1 was repeated to give aminated heparin in a yield of 642 mg.

Purity of aminated heparin: 90.3%.

Using 100 mg of this aminated heparin, a heparin-allyl compound was prepared in accordance with the procedure of Example 1. Thus 89.9 mg of the product was obtained.

Purity of heparin-allyl compound: 90.0%.

Optical rotation: 43.2 (1%, H$_2$O).

Figure 2:
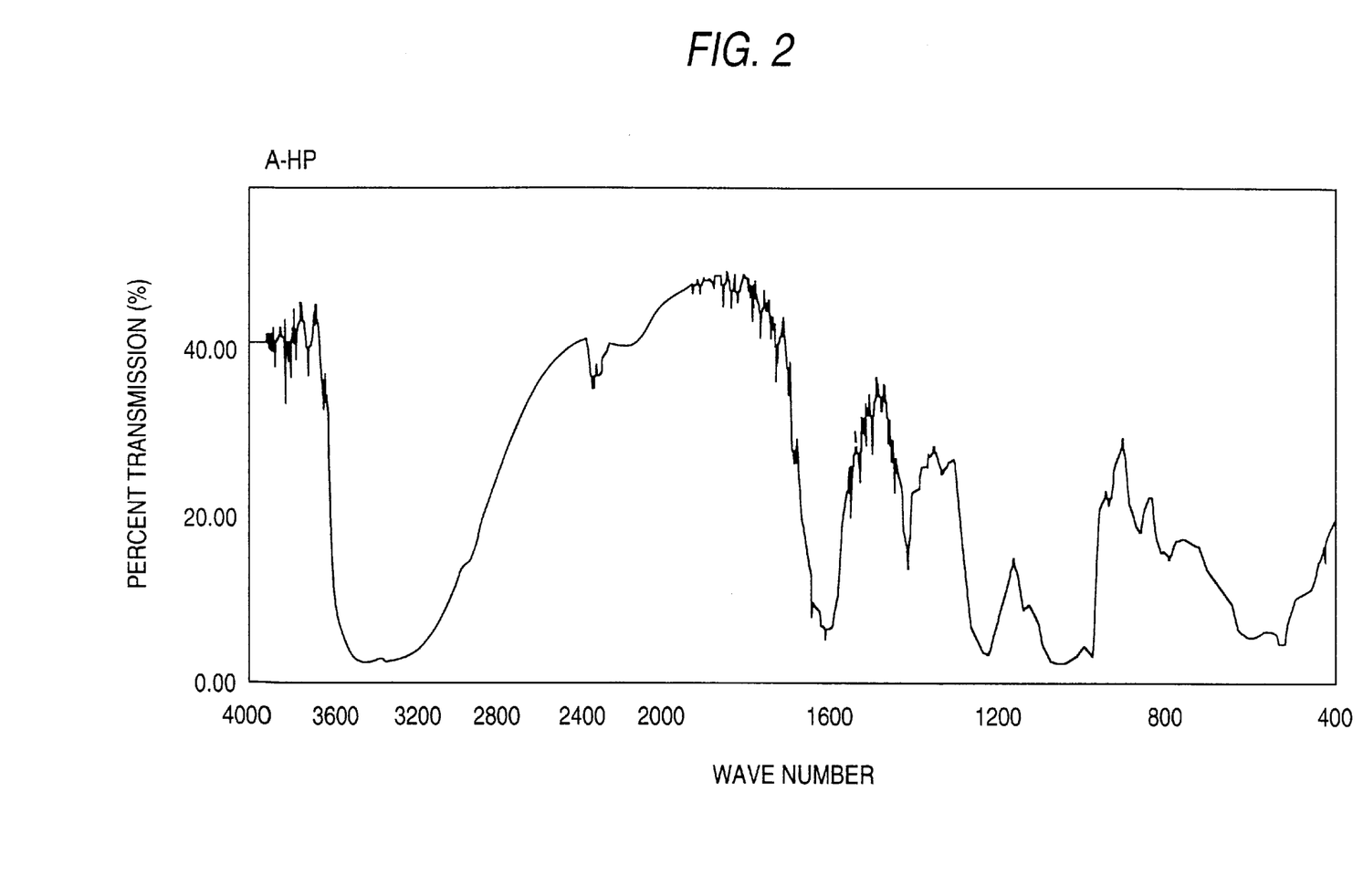
FIG. 2 is an IR spectrum of the heparin-allyl compound of the present invention.

FIG. 2 shows the IR spectrum of the heparin-allyl compound.

EXAMPLE 4

An apparatus commonly employed for polyacrylamide gel electrophoresis was prepared and two gel carriers having thickness of 1 mm were formed to have the following three compositions (a), (b) and (c). The first gel contains a 8.0% polyacrylamide gel as the composition (a), the polyacrylamide gel having chondroitin sulfate (8.5 μg/ml) homogeneously contained in (a) as the composition (b), and a 12.5% polyacrylamide gel as the composition (c). The second gel contains a 8.0% polyacrylamide gel as the composition (a), the polyacrylamide gel having the chondroitin sulfate-allyl compound synthesized in Example 1 (8.5 μg/ml) homogeneously contained in (a) as the composition (b), and a 12.5% polyacrylamide gel as the composition (c).

The gel solutions for preparing the polyacrylamide gels and the electrophoresis medium employed were as follows.

| | Polyacrylamide gel | |
|---|---|---|
| Reagent | 8.0% | 12.5% |
| 30% acrylamide stock solution (ml)[1)] | 8.0 | 12.5 |
| water (ml) | 18.8 | 14.8 |
| 10XTBE (ml)[2)] | 3.0 | 3.0 |
| 10% APS (ml)[3)] | 0.15 | 0.15 |
| TEMED (μl)[4)] | 5.0 | 5.0 |

[1)]30% acrylamide stock solution
acrylamide 58 g
N,N'-methylenebisacrylamide 2 g
water 200 ml
Filtered and stored at 4° C. (for several months).
[2)]Electrophoresis buffer (10XTBE buffer)
tris (powder) 108 g
boric acid 55 g
EDTA-2Na 9.3 g
water 1000 ml
Stored at room temperature.
Diluted 10-fold with water just prior to use.
[3)]10% APS (ammonium persulfate)
ammonium persulfate 0.4 g
water 4 ml
Prepared just prior to use.
[4)]TEMED: N,N,N',N'-tetramethylethylenediamine.

Electrophoresis was carried out under the following conditions.

Running buffer: 0.025 M tris, 0.192 M glycin (pH 8.3)-0.1% SDS

Sample buffer: Laemli's sample buffer

Running: 20 mA, for 100 minutes, at room temperature

Washing: 2.5% Triton X-100, for 1 hour, at room temperature

Incubation: 37° C., for 16 hours

Treatment with protease: 0.1 mg/ml of Pronase, for 2 hours, at 37° C.

Fixation: 20% EtOH-10% AcOH, for 20 minutes

Staining: 0.5% Alcian blue in 20% EtOH-10% ACOH, for 1 hour

Destaining: 20% EtOH-10% AcOH, for 1 hour×2

As a result, the chondroitin sulfate in the first gel which had been merely added to the gel was not stained, while the part (b) of the second gel according to the present invention was definitely stained. Based on these facts, it has been proved that the chondroitin sulfate merely added to the gel flew out during the electrophoresis while, in the gel of the present invention, the chondroitin sulfate was certainly fixed to the polyacrylamide gel.

EXAMPLE 5
Detection Limit of Chondroitinase ABC

Figure 3:
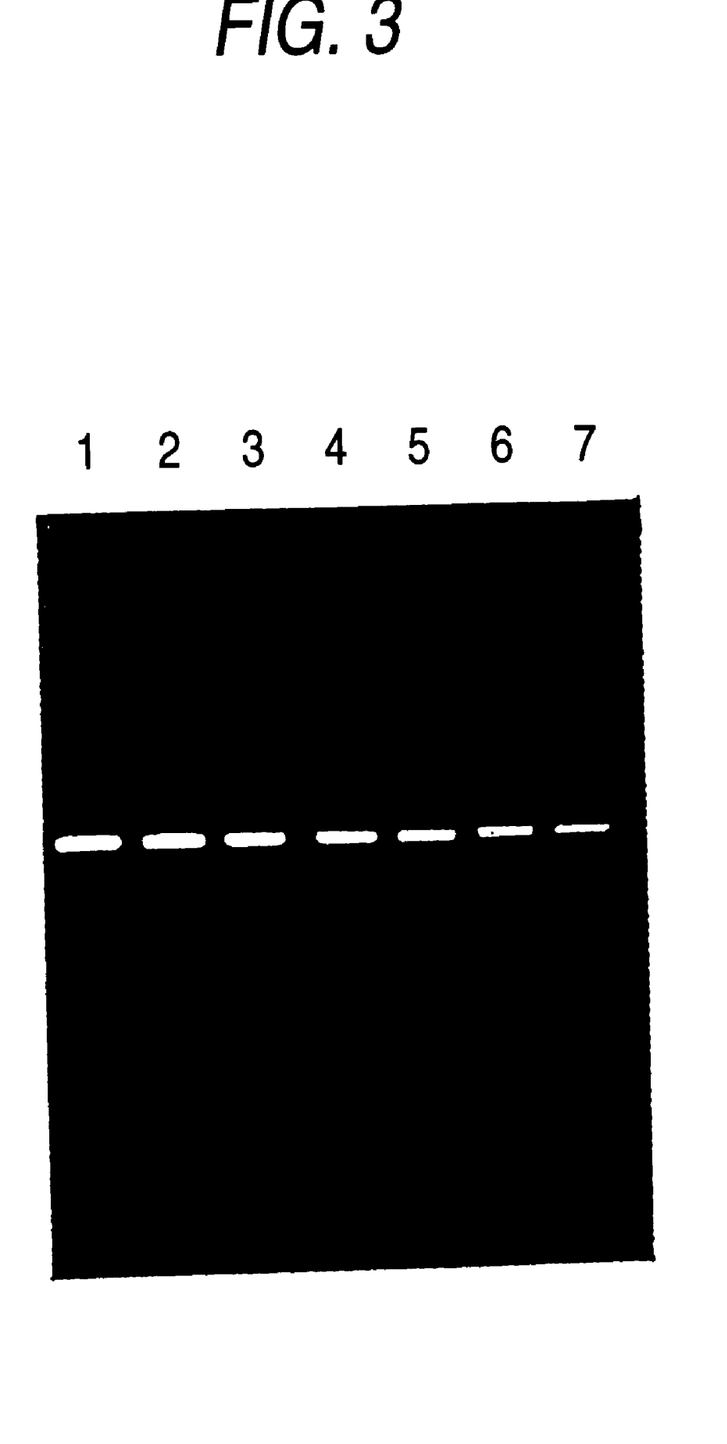
FIG. 3 is an electrophoretic pattern of Chondroitinase ABC (chondroitin sulfate-degrading enzyme originating in *Proteus vulgaris*, manufactured by Seikagaku Corporation). The lane numbers 1 to 7 respectively stand for the enzyme concentrations of 250 $\mu$U, 200 $\mu$U, 175 $\mu$U, 125 $\mu$U, 75 $\mu$U, 50 $\mu$U and 25 $\mu$U.

A 8.0% polyacrylamide gel for electrophoresis was prepared by using the chondroitin sulfate-allyl compound of the present invention synthesized in Example 1. In this Example, 0.1% (the final concentration) of sodium dodecyl sulfate (SDS) was added to the gel solution for preparing the 8.0% polyacrylamide gel described in Example 4. Chondroitinase ABC in various amounts was electrophoresed on this gel in the same manner as in Example 4 except that SDS was added to the electrophoresis buffer to give a final concentration of 0.1%. After electrophoresing at 20 mA, each gel was washed with 2.5% Triton X-100 at room temperature for 1 hour. Then it was incubated in a 50 mM citric acid-$Na_2HPO_4$ buffer (pH 6.0) containing 0.15 M of NaCl at 37° C. for 16 hours to thereby proceed the enzymatic reaction. Then, it was further incubated in a 20 mM tris-hydrochloride buffer (pH 8.0) containing 0.1 mg/ml of Pronase (originating in *Streptomyces griseus*, manufactured by Calbiochem) at 37° C. for 2 hours. Thereafter, it was incubated in 20% ethanol/10% acetic acid for 20 minutes and in 20% ethanol/10% acetic acid containing 0.5% of Alcian Blue for 1 hour for staining. Subsequently, it was incubated in 20% ethanol/10% acetic acid to thereby remove the excessive Alcian Blue. In the lane numbers 1 to 7 in FIG. 3, the following amounts of the enzyme were used:

1: 250 μU;
2: 200 μU;
3: 175 μU;
4: 125 μU
5: 75 μU;
6: 50 μU; and
7: 25 μU.

The term "1 U" as used herein means the amount of the enzyme capable of forming 1 μkmol of an unsaturated disaccharide from chondroitin 6-sulfate at pH 8.0 at 37° C. for 1 minute.

Thus it has been proved that even 25 μU of the enzyme can be detected, which indicates that the assay system achieve s high sensitivity.

EXAMPLE 6
Preparation of Dermatan Sulfate-allyl Compound

Starting from 15 g (1 mmol) of dermatan sulfate (molecular weight: 15,000), the procedure of Example 1 was repeated to give aminated dermatan sulfate in a yield of 15

Purity of aminated dermatan sulfate: 95.2%.

Using 100 mg of this aminated dermatan sulfate, a dermatan sulfate-allyl compound was prepared in accordance with the procedure of Example 1. Thus 98 mg of the product was obtained.

Purity of dermatan sulfate-allyl compound: 95.3%.

Figure 4:
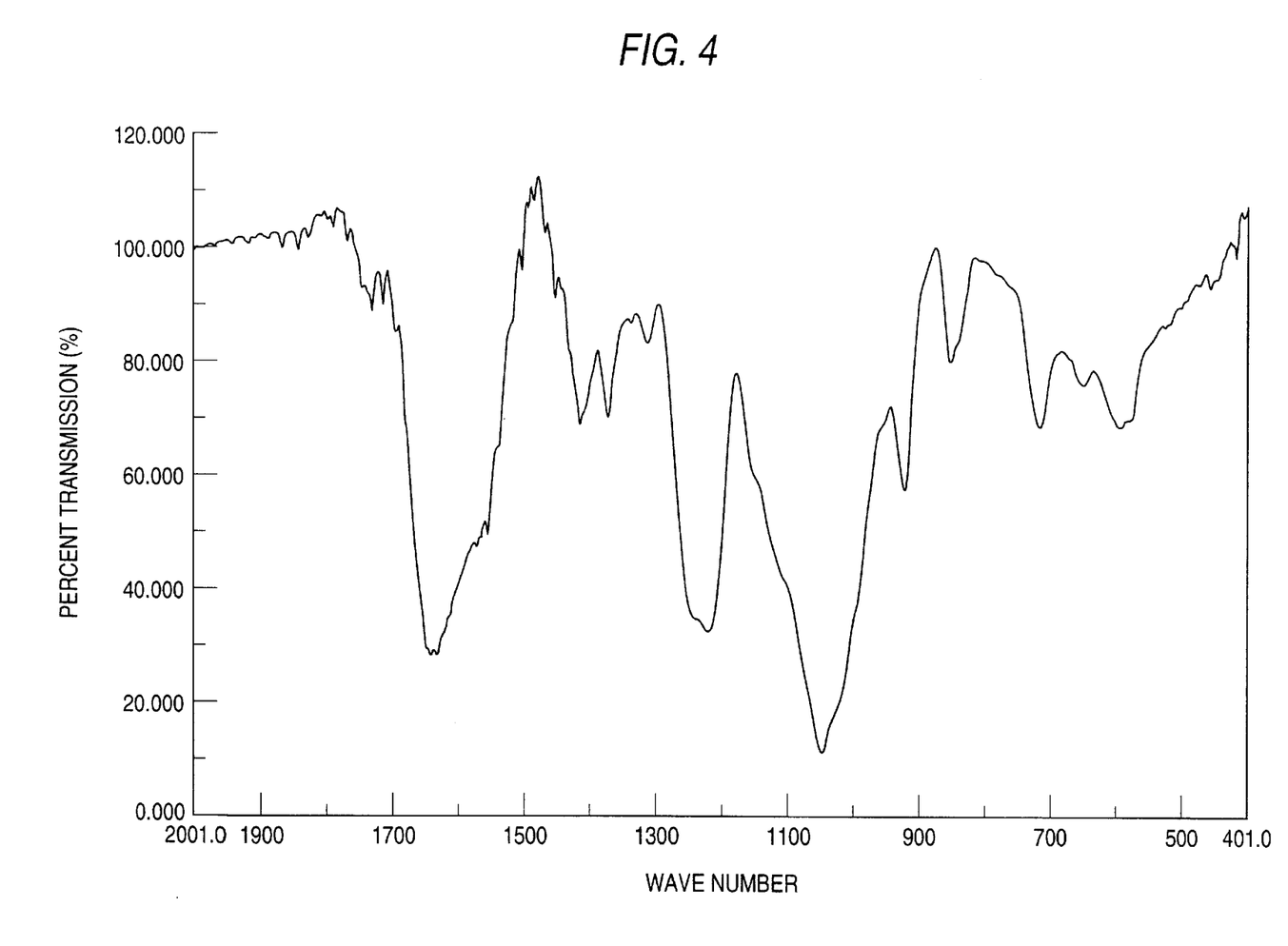
FIG. 4 is an IR spectrum of the dermatan sulfate-allyl compound of the present invention.

FIG. 4 shows the IR spectrum of the dermatan sulfate-allyl compound.

EXAMPLE 7
Preparation of Keratan Sulfate-allyl Compound

Starting from 80 mg (0.01 mmol) of keratan sulfate (molecular weight: 8,000), the procedure of Example 1 was repeated to give aminated keratan sulfate in a yield of 80 mg.

Purity of aminated keratan sulfate: 95.3%.

Using 80 mg of this aminated keratan sulfate, a keratan sulfate-allyl compound was prepared in accordance with the procedure of Example 1. Thus 78 mg of the product was obtained.

Purity of keratan sulfate-allyl compound: 96.0%.

Figure 5:
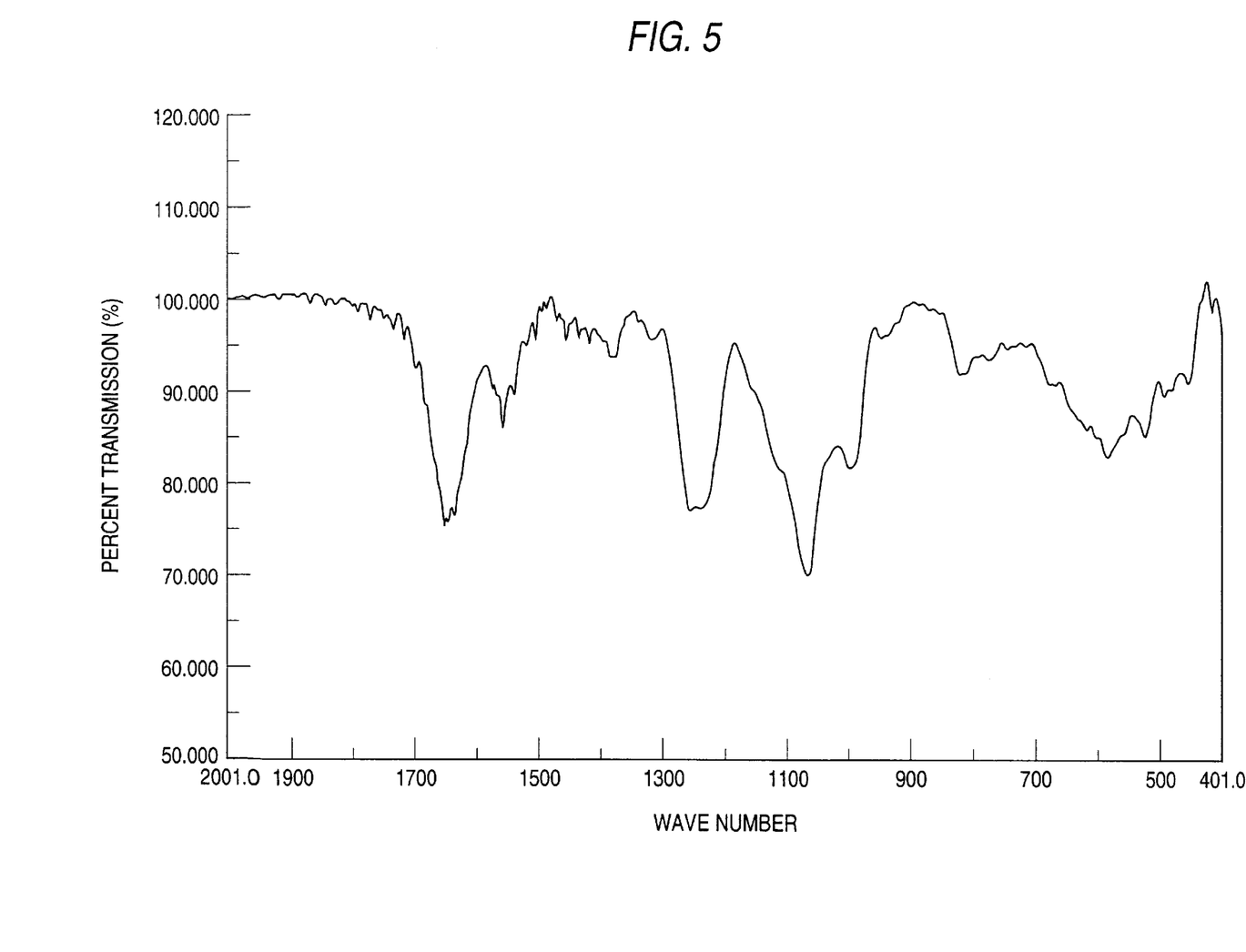
FIG. 5 is an IR spectrum of the keratan sulfate-allyl compound of the present invention.

FIG. 5 shows the IR spectrum of the keratan sulfate-allyl compound.

EXAMPLE 8
Preparation of Heparan Sulfate-allyl Compound

Starting from 100 mg (5 pmol) of heparan sulfate (molecular weight: 20,000), the procedure of Example 1 was repeated to give aminated heparan sulfate in a yield of 100 mg.

Purity of aminated heparan sulfate: 95.2%.

Using 80 mg of this aminated heparan sulfate, a heparan sulfate-allyl compound was prepared in accordance with the procedure of Example 1. Thus 75 mg of the product was obtained.

Purity of heparan sulfate-allyl compound: 95.0%.

Figure 6:
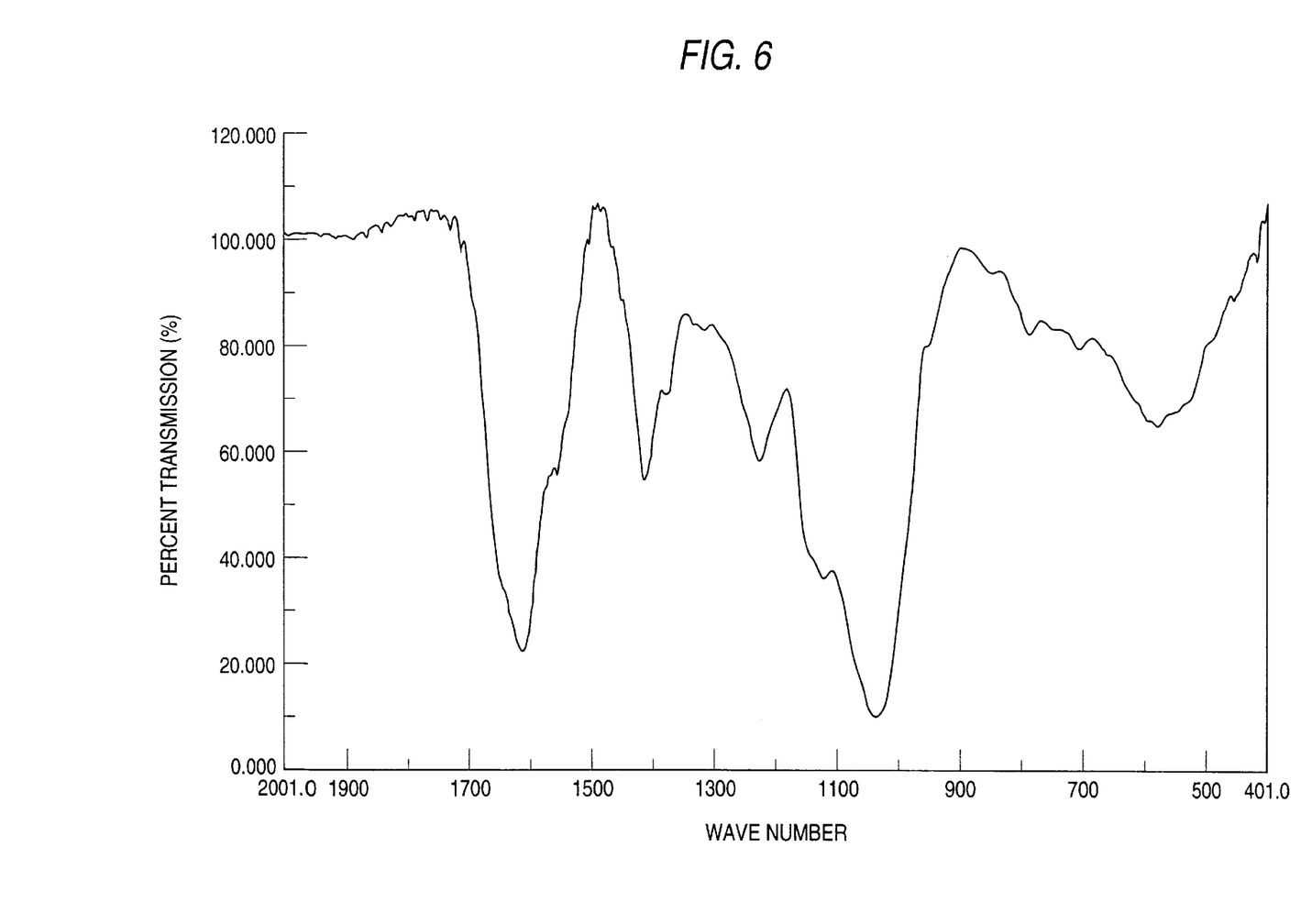
FIG. 6 is an IR spectrum of the heparan sulfate-allyl compound of the present invention.

FIG. 6 shows the IR spectrum of the heparan sulfate-allyl compound.

While the invention has been described in detail and with reference to specific embodiments thereof, it will be apparent to one skilled in the art that various changes and modifications can be made therein without departing from the spirit and scope thereof.

What is claimed is:

1. A glycosaminoglycan derivative represented by the formula (2):

$$GAG-R'-NHCH_2CH_2NHCH_2\underset{OH}{CH}-O-CH_2-CH=CH_2 \quad (2)$$

wherein GAG-R'—represents a glycosaminoglycan modified at the reducing end sugar; and R' represents $CH_2$ or CO.

2. A glycosaminoglycan derivative obtained by reacting:
   (a) a glycosaminoglycan;
   (b) a spacer compound of formula (1):

$$NH_2-Y-NH_2 \quad (1)$$

wherein Y represents —$[(CH_2)_n-(CHR)_m]$—, —$(CH_2)_x$—CH(COOH)—, phenylene or naphthylene; R represents H or an alkyl having 1 to 4 carbon atoms; x is an integer of 3 or 4; m is an integer of from 1 to 10; and n is an integer of from 1 to 10, provided that m+n is not more than 10; and
   (c) a hydrocarbon compound having a functional group at one end and an allyl group at another end, wherein said functional group is selected from the group consisting of an epoxy group, a halogen atom, a hydroxyl group, and a carboxyl group, wherein
   (1) said glycosaminoglycan is bonded to said spacer compound via an aminoalkyl bond obtained by reacting an aldehyde group, formed by reducing and partially oxidizing a reducing end sugar of said glycosaminoglycan, with a first amino group of said spacer compound, or
   (1') said glycosaminoglycan is bonded to said spacer compound via an acid amide bond obtained by reacting a lactone, formed by oxidizing and cyclodehydrating a reducing end sugar of said glycosaminoglycan, with said first amino group of said spacer compound, and further
   (2) said hydrocarbon compound is bonded to said spacer compound by reacting said functional group with a second amino group of said spacer compound.

3. The glycosaminoglycan derivative as claimed in claim 2, wherein said spacer compound is selected from the group consisting of ethylenediamine, 1,3-propanediamine, 1,4-butanediamine, 1,6-hexanediamine, 1,6-diamino-2-ethylhexane, 1,4-diaminobenzene, 1,4-diaminonaphthalene, 1,5-diaminonaphthalene, 2,7-diaminonaphthalene, lysine and ornithine.

4. The glycosaminoglycan derivative as claimed in claim 3, wherein said spacer compound is ethylenediamine.

5. The glycosaminoglycan derivative as claimed in claim 2, wherein said hydrocarbon compound is allylglycidyl ether.

6. The glycosaminoglycan derivative as claimed in claim 1 or 2, wherein the glycosaminoglycan is selected from the group consisting of hyaluronic acid, chondroitin, chondroitin sulfate, dermatan sulfate, heparin, keratan sulfate and heparan sulfate.

7. A glycosaminoglycan-bonded polyacrylamide gel, comprising the glycosaminoglycan derivative as claimed in claim 1 or 2 copolymerized with acrylamide.

8. The glycosaminoglycan-bonded polyacrylamide gel as claimed in claim 7, further comprising N,N'-methylenebisacrylamide copolymerized with said acrylamide.

9. The glycosaminoglycan-bonded polyacrylamide gel as claimed in claim 7, wherein the glycosaminoglycan is selected from the group consisting of hyaluronic acid, chondroitin, chondroitin sulfate, dermatan sulfate, heparin, keratan sulfate and heparan sulfate.

10. A gel electrophoresis carrier which comprises the glycosaminoglycan-bonded polyacrylamide gel as claimed in claim 7.

11. A method of preparing a glycosaminoglycan derivative comprising the steps of:

(a) reacting a first amino group of a spacer compound of formula (1) with (i) an aldehyde group, formed by reducing and partially oxidizing a reducing end sugar of a glycosaminoglycan, to form an aminoalkyl bond, or (ii) a lactone, formed by oxidizing and cyclodehydrating the reducing end sugar of a glycosaminoglycan, to form an acid amide bond, and (b) further reacting a functional group of a hydrocarbon compound with a second amino group of said spacer compound, wherein said hydrocarbon compound has an allyl group at one end and said functional group at another end, wherein said functional group is selected from the group consisting of an epoxy group, a halogen atom, a hydroxyl group, and a carboxyl group, $$NH_2-Y-NH_2 \qquad (1)$$

wherein Y represents $-[(CH_2)_n-(CHR)_m]-$, $-(CH_2)_x-CH(COOH)-$, phenylene or naphthylene; R represents H or an alkyl having 1 to 4 carbon atoms; x is an integer of 3 or 4, m is an integer of from 1 to 10; and n is an integer of from 1 to 10, provided that m+n is not more than 10.

12. The method of claim 11, wherein said spacer compound is selected from the group consisting of ethylenediamine, 1,3-propanediamine, 1,4-butanediamine, 1,6-hexanediamine, 1,6-diamino-2-ethylhexane, 1,4-diaminobenzene, 1,4-diaminonaphthalene, 1,5-diaminonaphthalene, 2,7-diaminonaphthalene, lysine and ornithine.

13. The method of claim 11, wherein said hydrocarbon compound is allylglycidyl ether.

14. The method of claim 11, wherein the glycosaminoglycan is selected from the group consisting of hyaluronic acid, chondroitin, chondroitin sulfate, dermatan sulfate, heparin, keratan sulfate and heparan sulfate.

* * * * *